United States Patent [19]

Ishii

[11] Patent Number: 4,794,804
[45] Date of Patent: Jan. 3, 1989

[54] SALT DAMAGE ENVIRONMENTAL TESTING CHAMBER FOR SELF-PROPELLED VEHICLES

[75] Inventor: Masanobu Ishii, Yokohama, Japan

[73] Assignee: Kabushiki-Kaisha Toyo Seisakusho, Tokyo, Japan

[21] Appl. No.: 23,460

[22] Filed: Mar. 9, 1987

[30] Foreign Application Priority Data

Feb. 19, 1987 [JP] Japan .................. 62-36677

[51] Int. Cl.⁴ .................................. G01N 17/00
[52] U.S. Cl. ..................................... 73/865.6
[58] Field of Search ............... 73/865.6, 29, 19, 431; 343/872; 324/61 R, 65 R; 204/428, 429; 374/209

[56] References Cited

U.S. PATENT DOCUMENTS

| 2,845,790 | 8/1958 | Eddy | 73/29 |
| 2,997,878 | 8/1961 | Graham | 324/61 R |
| 3,236,093 | 2/1966 | Werner | 73/431 |
| 3,259,466 | 7/1966 | Jacks, Jr. | 73/865.6 |
| 3,273,802 | 9/1966 | Hull, Jr. | 73/865.6 |
| 4,144,636 | 3/1979 | Burkhardt et al. | 204/15 |
| 4,489,590 | 12/1984 | Hadden | 73/1 G |

Primary Examiner—Stewart J. Levy
Assistant Examiner—Robert R. Raevis
Attorney, Agent, or Firm—Frishauf, Holtz, Goodman & Woodward

[57] ABSTRACT

A salt damage environmental testing chamber for self-propelled vehicles which is provided with a salt water spraying system, is disclosed. According to the present invention, a protective cover that may be opened and closed by a cover opening and closing device is provided in the vicinity of a humidty sensor provided in turn in the test chamber. The cover opening and closing device is actuated at the time of spraying of salt water into the test chamber to close the protective cover so that the humdity sensor is covered by the protective cover.

4 Claims, 3 Drawing Sheets

1

SALT DAMAGE ENVIRONMENTAL TESTING CHAMBER FOR SELF-PROPELLED VEHICLES

BACKGROUND OF THE INVENTION

1. Field of the Invention

This invention relates to a salt damage environmental testing chamber for self-propelled vehicles, especially automobiles.

2. Description of the Prior Art

In environmental tests for automobiles that are designed to run along the coast area and thus subject to corrosion due to salt damage, the vehicles are tested in a test chamber provided with a salt water spraying device.

The salt damage test chamber is provided with a temperature sensor for constantly measuring the temperature in the chamber and a humidity sensor for measuring the humidity in the chamber.

When conducting a test on the effect of the salt damage by spraying salt water into the chamber, the salt water adheres to the humidity sensor provided in the test chamber, making it impossible to perform humidity measurement. The humidity is measured with the air in the chamber coming into physical contact with the humidity sensitive portion of the sensor. Should the salt water adhere to it, the properties of the sensitive portion are lowered with repetition of the tests (since it is difficult to remove the moisture contents in the salt water) in such a manner that the follow-up properties and reproducibility of the humidity sensor are gradually lowered. As it becomes more difficult to measure the humidity in the test chamber, regular output signals can no longer be supplied from the humidity sensor to the humidity control unit adapted to control the humidity in the test chamber, so that it becomes more difficult to control the humidity in the chamber.

Note that the temperature sensor is not affected by the salt water.

SUMMARY OF THE INVENTION

One objective of the present invention is to provide a salt damage environmental testing chamber for self-propelled vehicles in which test the accuracy of the humidity sensor provided in the environmental testing chamber is not lessened by the salt water sprayed into the chamber for salt damage testing.

Another objective of the present invention to provide a test chamber in which humidity control can be made accurately.

In view of these objectives, the present invention provides a salt damage environmental testing chamber for self-propelled vehicles, in which a protective cover that may be opened and closed by a cover opening and closing device is provided in the vicinity of a humidity sensor in the test chamber., This cover opening and closing device is actuated at the time of the spraying of salt water into the test chamber to close the protective cover and protect the humidity sensor.

DESCRIPTION OF THE PREFERRED EMBODIMENTS

A preferred embodiment of the present invention will be hereafter explained by referring to the accompanying drawings.

Figure 1:
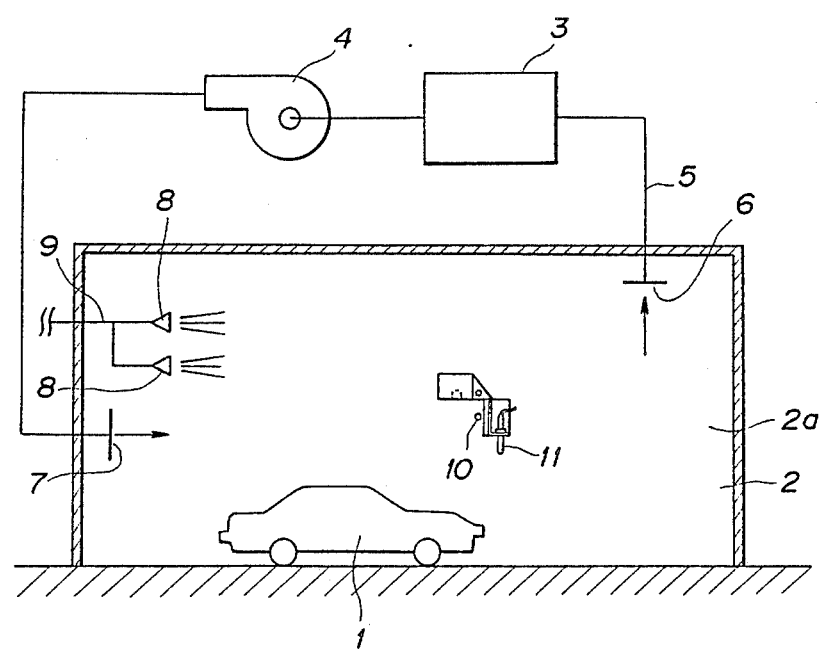
FIG. 1 is a diagrammatic view showing a salt damage environment test chamber according to an embodiment of the present invention.

Referring to FIG. 1, a self-propelled vehicle, such as an automobile 1, is shown in a salt damage environment test chamber 2, to which there are annexed an air conditioner 3 for setting the desired temperature and humidity in the test chamber and a blower 4 adjacent to the air conditioner.

The air conditioner 3 and the blower 4 are provided in an air circulation duct 5 having an inlet port 6 opening into the test chamber 2 and a discharge port 7 similarly opening into the test chamber 2.

A spray port 8 similarly opens into the test chamber 2 for spraying salt water into the test chamber when tests for salt damage are conducted. The spray port 8 is attached to the end of a piping 9 introduced from outside the test chamber 2.

A humidity sensor 10 and a temperature sensor 11 are located on, for example, a wall surface 2a in the test chamber 2, for measuring the humidity and the temperature in the test chamber 2.

Figure 2:
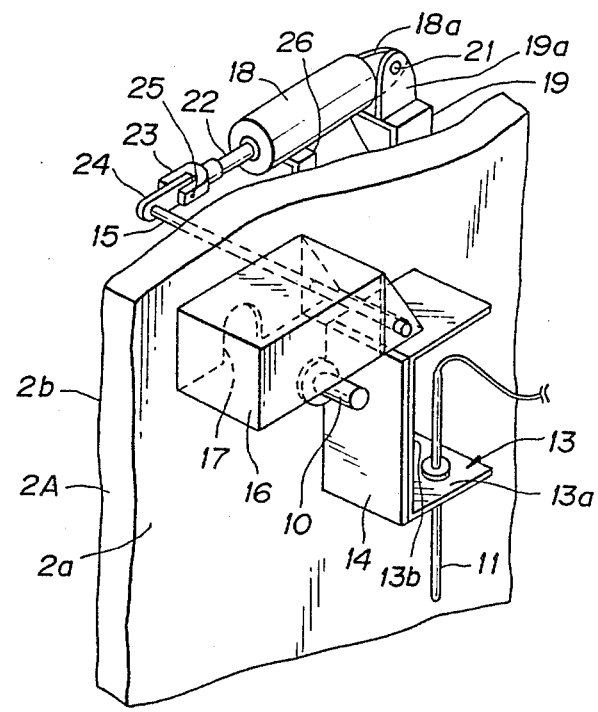
FIG. 2 is a partial perspective view showing essential parts of the test chamber shown in FIG. 1.
Figure 3:
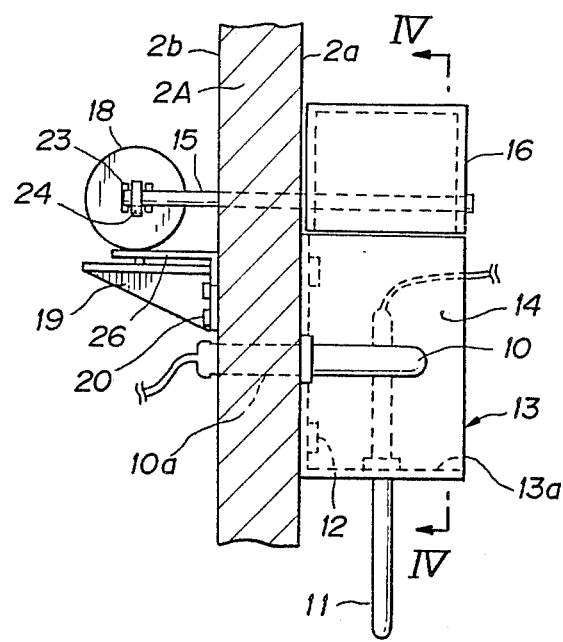
FIG. 3 is a side view of FIG. 2.

As shown in FIGS. 2 and 3, the humidity sensor 10 is attached orthogonally to the wall surface 2a and has its proximate portion 10a embedded in a wall member 2A forming the wall surface 2a. On this wall surface 2a, a humidity sensor attachment plate 13 is secured by a bolt 12 laterally of the humidity sensor 10. The temperature sensor 11 is attached orthogonally to a horizontal section 13a of the attachment plate 13. A sealing packing 14 is bonded to the surface of a vertical section 13b of the attachment plate 13 facing the humidity sensor 10.

Rotary shaft 15 is rotatably passed through the wall member and has a portion exposed in the test chamber to which 2A and has a portion exposed in the test chamber to which is secured one end of a protective cover 16 for the humidity sensor. A side plate 16a facing the wall surface of the protective cover in the form of a regular parallel-pipe is formed with a semicircular cut-out 17 to fit with the humidity sensor 10 when the cover 16 is turned towards the humidity sensor 10.

To the outdoor side wall surface 2b of the wall member 2A, there is secured with a bolt 20 a supporting member 19 adapted for supporting a sensor cover driving member, such as a hydraulic cylinder 18. To an upright section 19a of the supporting member 19, there is rotatably supported at pin 21 a rear projecting plate 18a of the hydraulic cylinder 18.

A convert yoke 23 is attached to the foremost part of a driving shaft 22 of the hydraulic cylinder 18. A crank arm 24 secured orthogonally to the outdoor side end of the rotary shaft 15 has its free end held by the connect yoke 23 and journaled at pin 25 for rotation by the connect yoke.

Figure 4:
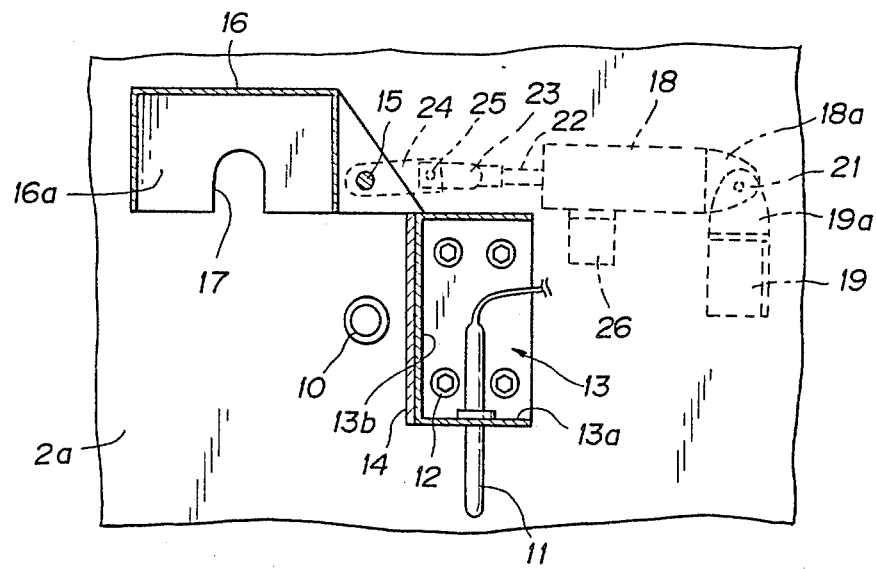
FIG. 4 is a sectional view taken along line 1V—1V of FIG. 3.

In operation, when the salt water is not being sprayed through the spray port 8, the drive shaft 22 is retracted into the inside of the hydraulic cylinder 18, so that the protective cover 16 is maintained in the horizontal position, as shown in FIG. 4. In this state, since the humidity sensor 10 is not covered by the protective cover, the humidity in the test chamber 2 can be measured by the humidity sensor 10. At this time, the forward part of the hydraulic cylinder 18 rests on a holding plate 26 secured to the wall surface 2b. The straight line connecting a line of extension of the driving shaft 22 and the crank arm 24 is above a horizontal line passing through the journal point of the cylinder.

Figure 5:
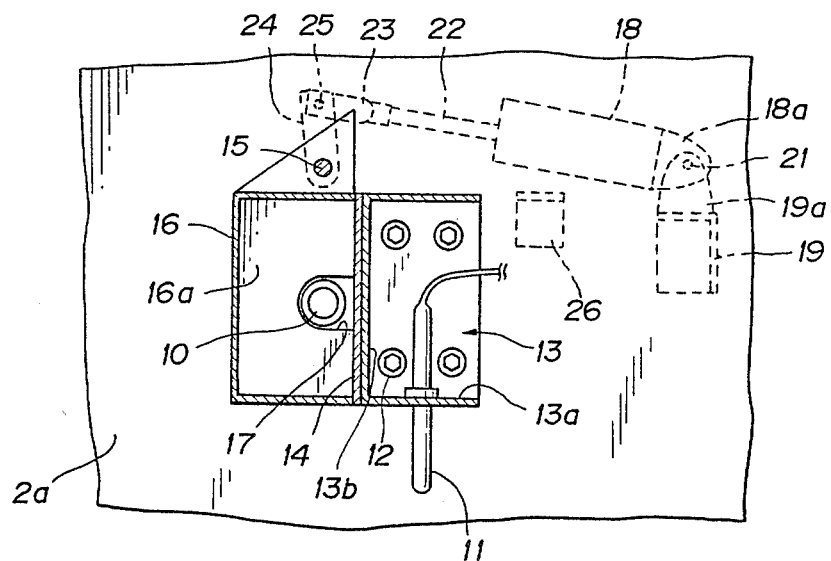
FIG. 5 is a sectional view similar to FIG. 4 but with the protective cover closed.

When the salt water is sprayed from the port 8 into the inside of the test chamber 2, the hydraulic cylinder 18 is actuated so that the drive shaft 22 is thrust forward. In this manner, the crank arm 24 is turned counter-clockwise in FIG. 5, so that the protective cover 16 attached to the rotary shaft 15 is turned counter-clockwise until it abuts on the packing 14 bonded to the attached plate 13. At this time, the humidity sensor 10 is covered by the now closed protective cover 16 so that there is no risk of the salt water adhering to the humidity sensor 10.

After termination of the spraying of the salt water, the protective cover 16 is opened as shown in FIG. 4 and the humidity in the test chamber is measured by the humidity sensor 10. The humidity in the chamber may be set to the desired design value on the basis of the sensor output.

By repetition of the above described procedure, the humidity in the environment test chamber 2 can be controlled without adverse effects due to the spraying of salt water.

It will be seen from the foregoing that the present invention provides for highly accurate humidity control in the test chamber 2 without lessening the accuracy of the humidity sensor 10 by the spraying of salt water.

What is claimed is:

1. A salt-damage environmental testing chamber comprising:
 a chamber;
 means within the chamber and coupled thereto for spraying salt water into the interior of the chamber;
 a humidity sensor within the chamber and coupled thereto;
 an enclosure surrounding said humidity sensor and including a base fixed to the chamber and a cover movable relative to said base between a closed position enclosing said humidity sensor within the enclosure and an open position exposing said humidity sensor; and
 means for moving said cover between its open and closed positions;
 wherein said base is fixed to a wall of said chamber, and said moving means comprises a shaft rotatably journalled in said wall and having a first portion extending into said chamber and a second portion extending outside of said chamber, said cover being attached to said first portion of the shaft.

2. The testing chamber of claim 1, wherein said moving means comprises a driving means outside of said chamber and coupled to the second portion of said shaft for rotating said shaft.

3. The testing chamber of claim 2, wherein said humidity sensor is fixed to said chamber wall and extends orthogonally thereto, said cover having a side adjacent said wall with a portion defining a recess accommodating said humidity sensor therein when the cover is in its closed position.

4. A salt-damage environmental testing chamber comprising:
 a chamber;
 means within the chamber and coupled thereto for spraying salt water into the interior of the chamber;
 a humidity sensor within the chamber and coupled thereto;
 an enclosure surrounding said humidity sensor and including a base fixed to the chamber and a cover movable relative to said base between a closed position enclosing said humidity sensor within the enclosure and an open position exposing said humidity sensor; and
 means for moving said cover between its open and closed positions,
 wherein said humidity sensor has one end fixed to a wall of said chamber and extends perpendicularly thereto to terminate at its remote end, said base being positioned laterally adjacent of said humidity sensor with said humidity sensor extending transversely across said base, and said cover having one side extending further away from said wall than the remote end of said humidity sensor and a second side being at a lesser distance from the wall than said remote end of the humidity sensor, said second side having a cut-out portion at an edge thereof facing the humidity sensor and accommodating the humidity sensor therein when the cover is in its closed position.

* * * * *